United States Patent
Nakamura et al.

(10) Patent No.: US 8,593,162 B2
(45) Date of Patent: Nov. 26, 2013

(54) FUEL-ASPECT SENSOR

(75) Inventors: Hiroshi Nakamura, Nishio (JP); Akikazu Uchida, Obu (JP)

(73) Assignee: Denso Corporation, Kariya (JP)

( * ) Notice: Subject to any disclaimer, the term of this patent is extended or adjusted under 35 U.S.C. 154(b) by 378 days.

(21) Appl. No.: 12/637,237

(22) Filed: Dec. 14, 2009

(65) Prior Publication Data

US 2010/0156443 A1 Jun. 24, 2010

(30) Foreign Application Priority Data

Dec. 19, 2008 (JP) ................................. 2008-324024

(51) Int. Cl.
*G01R 27/26* (2006.01)

(52) U.S. Cl.
USPC ........... 324/663; 324/698; 324/665; 324/670; 324/684; 324/685; 324/686; 324/690; 73/53.01; 73/53.05; 73/114.43; 73/114.41

(58) Field of Classification Search
USPC ......... 324/663, 698, 665, 670, 684, 685, 686, 324/690; 73/50.01, 53.05, 114.43, 114.41
See application file for complete search history.

(56) References Cited

U.S. PATENT DOCUMENTS

| | | | | |
|---|---|---|---|---|
| 2,438,550 A * | 3/1948 | Eritzman | ...................... | 324/464 |
| 3,044,453 A * | 7/1962 | Hoffmann | ................... | 123/25 R |
| 3,264,557 A * | 8/1966 | Heeps | ........................... | 324/695 |
| 3,527,268 A * | 9/1970 | Ginsburgh | ..................... | 141/98 |
| 4,074,184 A * | 2/1978 | Dechene et al. | ............... | 324/434 |
| 4,172,925 A * | 10/1979 | Chen et al. | ..................... | 429/111 |
| 4,517,547 A * | 5/1985 | Gray et al. | ..................... | 340/438 |
| 4,939,467 A * | 7/1990 | Nogami et al. | ............... | 324/663 |
| 4,939,468 A * | 7/1990 | Takeuchi | ....................... | 324/690 |
| 5,005,402 A * | 4/1991 | Pischinger et al. | ............ | 324/663 |
| 5,089,783 A * | 2/1992 | Kapsokavathis et al. | ...... | 324/672 |
| 5,124,654 A * | 6/1992 | Scheid | ........................... | 324/658 |
| 5,124,655 A * | 6/1992 | Takeuchi et al. | ............... | 324/690 |
| 5,134,381 A * | 7/1992 | Schmitz et al. | ............... | 324/685 |
| 5,182,523 A * | 1/1993 | Ertel et al. | ..................... | 324/663 |
| 5,182,942 A * | 2/1993 | Hartel et al. | .................. | 73/61.46 |
| 5,196,801 A * | 3/1993 | Nogami et al. | ............... | 324/663 |

(Continued)

FOREIGN PATENT DOCUMENTS

| JP | H01-163862 | 11/1989 |
|---|---|---|
| JP | H04-110969 | 9/1992 |

(Continued)

OTHER PUBLICATIONS

Japanese Office Action in corresponding JP App. No. 2008-324024, dated Jul. 2, 2012, with English translation.

*Primary Examiner* — Arleen M Vazquez
*Assistant Examiner* — Lamarr Brown
(74) *Attorney, Agent, or Firm* — Nixon & Vanderhye P.C.

(57) ABSTRACT

An object of the invention is to provide a fuel-aspect sensor having higher detection accuracy. A first electrode is inserted into a hole formed in a first housing member. A cylindrical second electrode is inserted into and firmly fixed to the first electrode by a cylindrical insulating member. A first elastic member, for example, made of rubber, is arranged between the first electrode and a second housing member. The first electrode has a large-diameter portion, which is biased by the first elastic member toward a sealing surface formed on an inner wall of the hole, so as to fluid-tightly seal a space between the first electrode and the second housing member.

7 Claims, 3 Drawing Sheets

(56) References Cited

U.S. PATENT DOCUMENTS

| | | | |
|---|---|---|---|
| 5,337,017 A * | 8/1994 | Ogawa | 324/682 |
| 5,337,018 A * | 8/1994 | Yamagishi | 324/693 |
| 5,361,035 A * | 11/1994 | Meitzler et al. | 324/663 |
| 5,414,367 A * | 5/1995 | Ogawa | 324/663 |
| 5,414,368 A * | 5/1995 | Ogawa et al. | 324/675 |
| 5,543,722 A * | 8/1996 | Suzuki et al. | 324/675 |
| 5,592,098 A * | 1/1997 | Suzuki et al. | 324/663 |
| 5,594,163 A * | 1/1997 | Suzuki | 73/61.44 |
| 5,672,324 A * | 9/1997 | Okamoto et al. | 422/174 |
| 6,057,693 A * | 5/2000 | Murphy et al. | 324/663 |
| 6,129,895 A * | 10/2000 | Edmondson | 422/78 |
| 6,500,571 B2 * | 12/2002 | Liberatore et al. | 429/2 |
| 6,566,892 B2 * | 5/2003 | Schaefer et al. | 324/663 |
| 6,629,521 B1 * | 10/2003 | Kato | 123/687 |
| 6,690,180 B2 * | 2/2004 | Schwartz et al. | 324/670 |
| 6,698,278 B2 * | 3/2004 | Zhang et al. | 73/61.76 |
| 6,836,123 B1 * | 12/2004 | Qi et al. | 324/446 |
| 7,030,629 B1 * | 4/2006 | Stahlmann et al. | 324/663 |
| 7,168,300 B2 * | 1/2007 | Kawanishi et al. | 73/61.46 |
| 7,775,092 B2 * | 8/2010 | Murphy et al. | 73/114.38 |
| 8,072,229 B2 * | 12/2011 | Nakamura et al. | 324/663 |
| 8,264,243 B2 * | 9/2012 | Tarui et al. | 324/663 |
| 2002/0189335 A1 * | 12/2002 | Matsumura et al. | 73/118.1 |
| 2003/0117153 A1 * | 6/2003 | McKenzie et al. | 324/663 |
| 2003/0230856 A1 * | 12/2003 | Forry et al. | 277/592 |
| 2004/0004487 A1 * | 1/2004 | Vanzuilen et al. | 324/663 |
| 2004/0055580 A1 * | 3/2004 | Yamada et al. | 123/495 |
| 2004/0183552 A1 * | 9/2004 | Aghamehdi et al. | 324/690 |
| 2004/0255647 A1 * | 12/2004 | Lin et al. | 73/53.01 |
| 2005/0090805 A1 * | 4/2005 | Shaw et al. | 604/523 |
| 2005/0248358 A1 * | 11/2005 | Boyle et al. | 324/698 |
| 2006/0137340 A1 * | 6/2006 | Stewart | 60/599 |
| 2006/0179928 A1 * | 8/2006 | Shikama et al. | 73/118.1 |
| 2006/0243939 A1 * | 11/2006 | Seko | 251/129.19 |
| 2007/0084274 A1 * | 4/2007 | Takayanagi | 73/118.1 |
| 2007/0179700 A1 * | 8/2007 | Nakamura | 701/103 |
| 2007/0193345 A1 * | 8/2007 | Yamamoto et al. | 73/61.41 |
| 2007/0214872 A1 * | 9/2007 | Ammann et al. | 73/53.01 |
| 2008/0029156 A1 * | 2/2008 | Rosal et al. | 137/2 |
| 2008/0143347 A1 * | 6/2008 | Casey et al. | 324/663 |
| 2008/0262321 A1 * | 10/2008 | Erad et al. | 600/301 |
| 2008/0282779 A1 * | 11/2008 | Noguchi et al. | 73/53.01 |
| 2009/0090337 A1 * | 4/2009 | Asanuma et al. | 123/574 |
| 2009/0100907 A1 * | 4/2009 | Mizutani et al. | 73/31.05 |
| 2009/0100911 A1 * | 4/2009 | Kawanishi et al. | 73/61.43 |
| 2009/0153154 A1 * | 6/2009 | Hernandez et al. | 324/698 |
| 2009/0193873 A1 * | 8/2009 | Nakamura et al. | 73/31.05 |
| 2009/0301045 A1 * | 12/2009 | Nelson et al. | 55/498 |

FOREIGN PATENT DOCUMENTS

| | | |
|---|---|---|
| JP | 6-46367 | 6/1994 |
| JP | 2000-009673 | 1/2000 |
| JP | 2006-317214 | 11/2006 |
| JP | 2007-120962 | 5/2007 |

* cited by examiner

FUEL-ASPECT SENSOR

CROSS REFERENCE TO RELATED APPLICATION

This application is based on Japanese Patent Application No. 2008-324024 filed on Dec. 19, 2008, the disclosure of which is incorporated herein by reference.

FIELD OF THE INVENTION

The present invention relates to a sensor for detecting fuel aspect based on electrostatic capacity of the fuel.

BACKGROUND OF THE INVENTION

In a conventional vehicle using ethanol-mixed gasoline, ethanol density contained in fuel is detected so as to adjust fuel injection amount as well as fuel injection timing in accordance with detected ethanol density, so that deterioration of exhaust gas is suppressed and adverse affect to vehicle drivability is decreased.

According to a prior art, such as U.S. Pat. No. 7,030,629, electrostatic capacity between a first electrode forming a fluid passageway and a second electrode supported within the fluid passageway is detected, and ethanol density contained in fuel is detected based on detected value for the electrostatic capacity, wherein the detected value for the electrostatic capacity is corrected by fuel temperature detected by a temperature sensor.

According to such a fluid quality sensor, however, heat generated at an electric circuit for detecting the ethanol density as well as heat from ambient atmosphere may be transmitted to the temperature sensor through an inside of a sensor housing. Therefore, there is a concern that such heat transfer may adversely affect detection value of the temperature sensor. In the case that an error may occur in the detection value, detection accuracy for the ethanol density may be decreased.

In addition, there may be another concern that a glass seal for insulating between the first and second electrodes may be broken or a crack may be generated in the glass seal, for example, due to mechanical shock during product transportation or a product assembling process. When the glass seal was broken, there would be a possibility that fuel may leak from the fuel passageway.

Furthermore, there is a concern that electric conductive members, which connect the first and second electrodes and the electric circuit with each other, may be disconnected due to different coefficients of thermal expansion between the housing for the electric circuit and the first and second electrodes. In such a case (disconnection of electric conductive members), it becomes impossible to detect the electrostatic capacity.

SUMMARY OF THE INVENTION

The present invention is made in view of the above problems. It is an object of the present invention to provide a fuel-aspect sensor, in which detection accuracy for detecting aspect of fuel is improved.

According to a feature of the invention, a fuel-aspect sensor is composed of the following components;

a first housing member having a fuel chamber through which fuel flows and an insertion hole for communicating the fuel chamber with outside of the first housing member;

a first electrode inserted into the insertion hole from an open end of the insertion hole, the first electrode having an inside space being in communication with the fuel chamber;

a second electrode having a closed bottom portion, a lower part of the second electrode being accommodated in the inside space of the first electrode, so that an outer surface of the second electrode is exposed to the fuel introduced into the inside space of the first electrode;

an insulating member for electrically insulating the first and second electrodes from each other and firmly fixing the first and second electrodes to each other;

a temperature sensor accommodated in the second electrode and fixed to an inside surface of the closed bottom portion thereof;

a second housing member firmly attached to the first housing member for closing the open end of the insertion hole of the first housing member;

an electronic control unit accommodated in the second housing member and electrically connected to the first electrode, the second electrode, and the temperature sensor, for detecting electrostatic capacity between the first and second electrodes; and an elastic member disposed between the second housing member and the first electrode for biasing the first electrode toward a sealing surface of the first housing member, which is formed at an inner wall of the insertion hole so as to oppose to the open end of the insertion hole.

According to the above feature of the invention, the elastic member can suppress a possible generation of a gap, which may be generated between the second housing member and the first electrode due to their different coefficients of thermal expansion. As a result, it is possible to prevent a disconnection of a terminal (an electric conductive member), which connects the first electrode to the electronic control unit (that is, an electric circuit).

In addition, the elastic member can absorb mechanical shock, which may be applied to the insulating member from the second housing member via the first electrode, in a case that any external force may be applied to the second housing member, for example, in a case that the sensor is dropped during transportation or an assembling process. As a result, it is possible to prevent the insulating member (such as, glass seal) from being broken or prevent a crack from being generated in the insulating member.

Furthermore, the elastic member suppresses thermal conduction between the second housing member and the first electrode, so that heat generated at the electronic control unit (the electric circuit) to the temperature sensor via the second housing member, the first electrode, the insulating member, and the second electrode can be prevented. As a result, the temperature sensor accurately detects the temperature of the fuel between the first and second electrodes, wherein the heat of the fuel is transmitted to the temperature sensor via the second electrode. Accordingly, the detection accuracy for detecting the aspect of fuel can be improved.

According to another feature of the invention, the elastic member is made of such material having coefficient of thermal conductivity smaller than those of the second housing member and the first electrode. As a result, the elastic member can surely prevent the heat transfer between the second housing member and the first electrode.

According to a further feature of the invention, the sealing surface of the first housing member is formed as a stepped surface at the inner wall of the insertion hole, which is perpendicular to a direction in which the first electrode is biased by the elastic member. As a result, the elastic member can surely bias the first electrode to the sealing surface (the stepped surface) of the first housing member.

According to a still further feature of the invention, the elastic member is accommodated in a recess formed at an outer bottom surface of the second housing member, and a circular hole is formed in the elastic member, through which an open-end side of the second electrode is inserted, so that an inner surface of the circular hole is fluid-tightly in contact with a radially-outward wall of the open-end side of the second electrode. As a result, it is possible to prevent the fuel from leaking to the electric circuit through a space between the second housing member and the second electrode.

According to a still further feature of the invention, the insulating member (such as, the glass seal) is formed in a cylindrical shape, and a ring-shaped elastic member is arranged at a position, which is away from the insulating member in a radially-outward direction, and the ring-shaped elastic member is arranged between the first electrode and the first housing member. As a result, the ring-shaped elastic member can prevent the fuel from leaking through a space between the first housing member and the first electrode.

In addition, the ring-shaped elastic member can absorb mechanical shock applied to the first electrode from the first housing member, when any external force may be applied to the first housing member. As a result, it is possible to prevent the insulating member (such as, the glass seal) from being broken or prevent a crack from being generated in the insulating member. Therefore, it is possible to prevent the fuel from leaking from a fuel passage to the electric circuit.

Furthermore, the ring-shaped elastic member suppresses thermal conduction between the first housing member and the first electrode. Namely, the heat generated at the electric circuit may be suppressed from being transmitted to the temperature sensor via the second housing member, the first housing member, the first electrode, the insulating member, and the second electrode. As a result, the temperature sensor accurately detects the temperature of the fuel, wherein the heat of the fuel is transmitted to the temperature sensor via the second electrode.

According to a still further feature of the invention, the fuel pipes for supplying the fuel into the fuel chamber and discharging the fuel from the fuel chamber are provided to the first housing member. Therefore, when a configuration of the fuel pipes is changed, the fuel-aspect sensor of the invention may be applied to various vehicle models. Namely, the same configurations of the first and second electrodes can be applied to different vehicle models. As a result, the detection accuracy of the sensor for detecting the aspect of fuel can be improved.

BRIEF DESCRIPTION OF THE DRAWINGS

The above and other objects, features and advantages of the present invention will become more apparent from the following detailed description made with reference to the accompanying drawings. In the drawings.

DETAILED DESCRIPTION OF THE PREFERRED EMBODIMENTS (First Embodiment)

Embodiments of the present invention will be explained with reference to the drawings.

Figure 1:
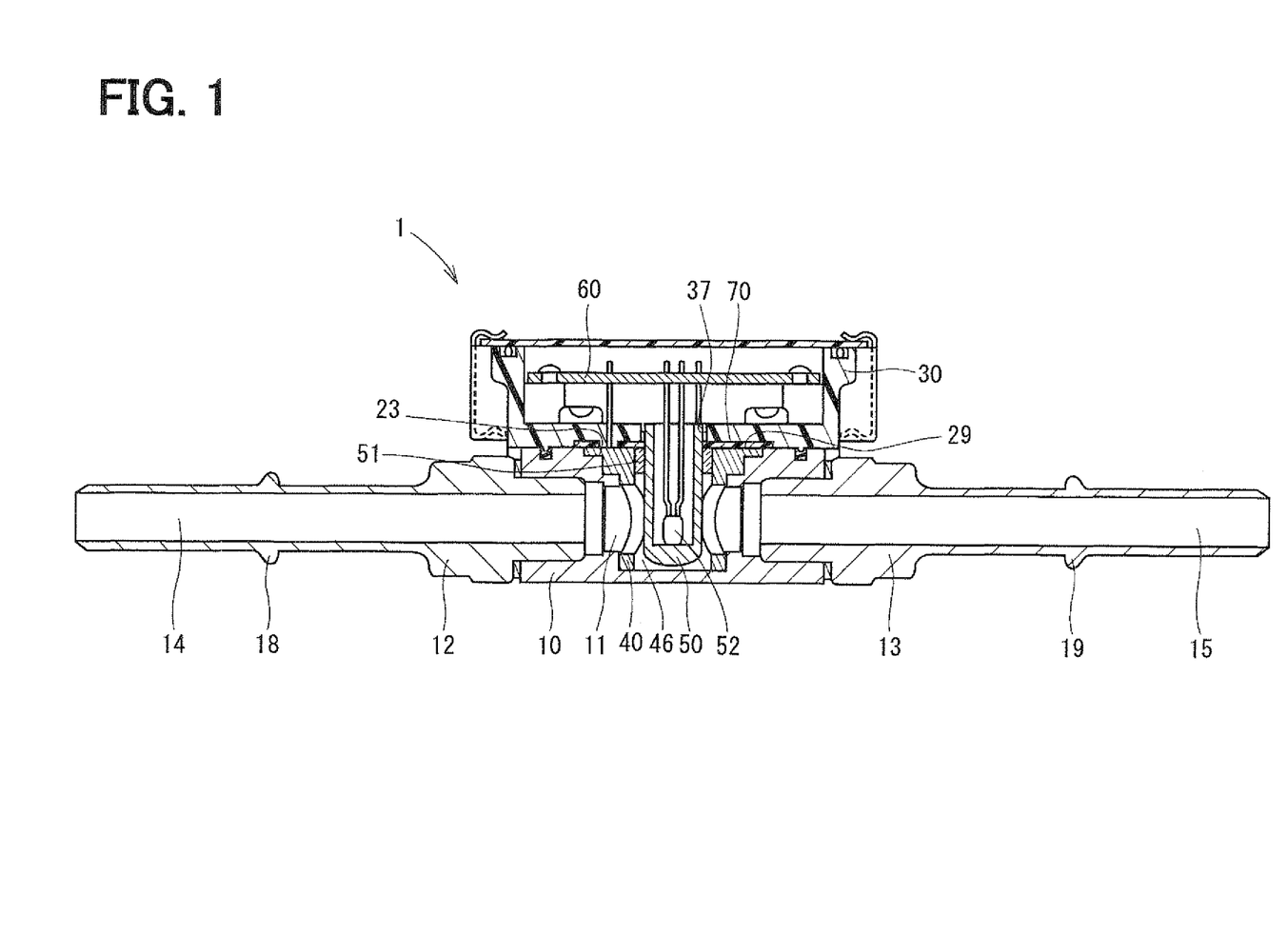
FIG. 1 is a schematic cross-sectional view showing a fuel-aspect sensor according to a first embodiment of the present invention.
Figure 2:
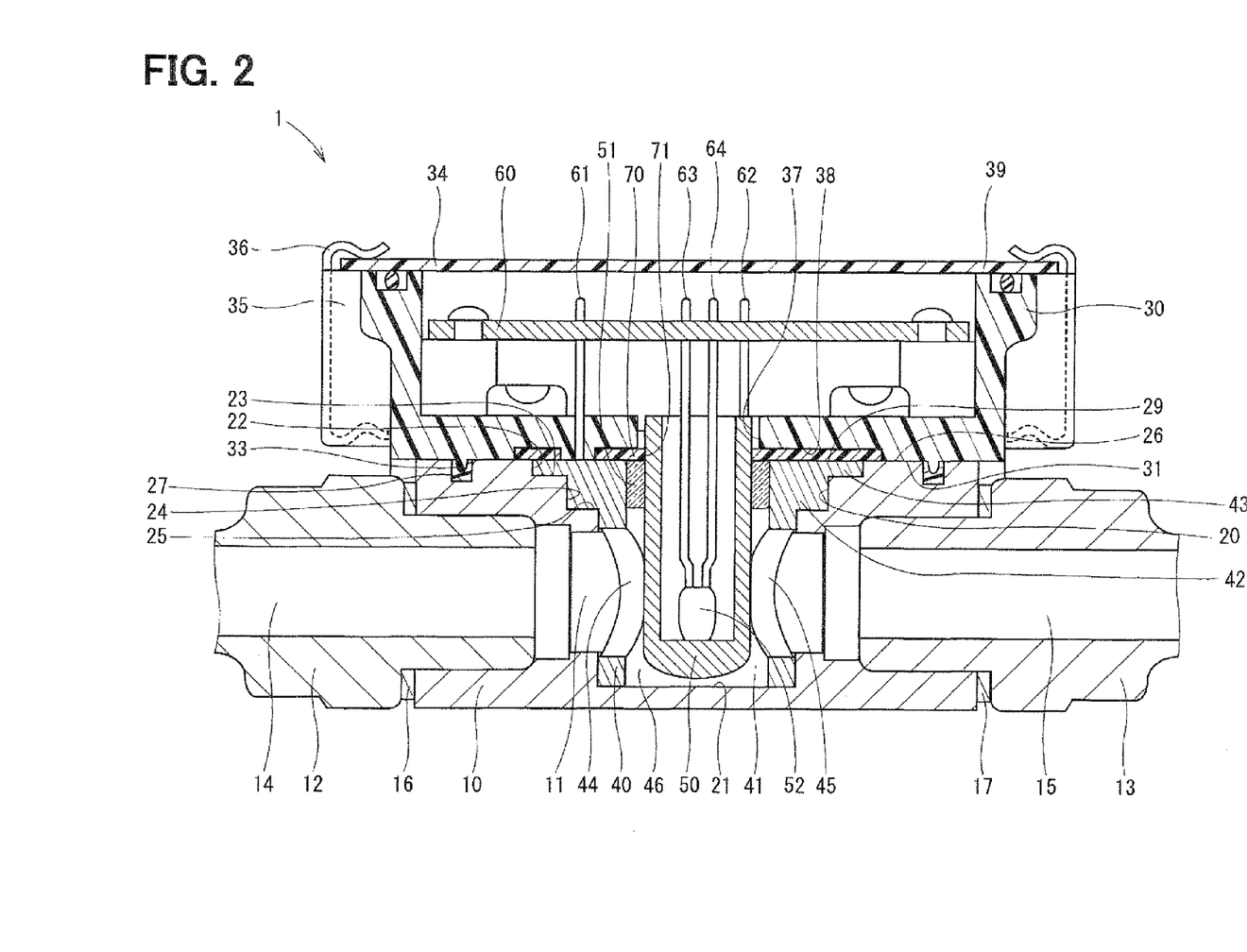
FIG. 2 is a schematic enlarged cross-sectional view showing a relevant portion of the fuel-aspect sensor according to the first embodiment.

FIGS. 1 and 2 show a fuel-aspect sensor 1 according to a first embodiment of the present invention. The fuel-aspect sensor 1 of the invention is provided between a fuel tank of a vehicle and a fuel injector for detecting ethanol density contained in fuel. The ethanol density detected by the fuel-aspect sensor is inputted into an engine control unit (hereinafter also referred to as ECU) and the ECU controls fuel injection amount to be injected by the fuel injector as well as fuel injection timing based on the detected ethanol density. Vehicle drivability is thus maintained at a higher value and harmful components contained in exhaust gas are decreased.

The fuel-aspect sensor 1 is composed of a first housing member 10, a second housing member 30, a first electrode 40, a second electrode 50, a thermistor (a temperature sensor) 52, an electric circuit (an electronic control unit) 60, and so on.

The first housing member 10 is made of metal, such as stainless steel or resin, and the first housing member 10 is formed in a cylindrical shape. A fuel chamber 11 is formed inside the first housing member 10.

Fuel pipes 12 and 13 are respectively connected to each axial end (e.g., a first axial end and a second axial end) of the first housing member 10. Each of the fuel pipes12 and 13 is made of metal, such as stainless steel, and is formed in a pipe-shape. Fuel passages 14 and 15 are respectively formed inside the fuel pipes 12 and 13. The fuel pipes 12 and 13 are formed in such shapes, so that the fuel pipes 12 and 13 are adapted to a fuel system of a vehicle to which the fuel-aspect sensor 1 is applied. Each of the fuel pipes 12 and 13 is connected (for example, screwed) to the first housing member 10 via sealing members 16 and 17 made of cupper, for example. Claws 18 and 19 are formed at outer surfaces of the fuel pipes 12 and 13, at each of longitudinal intermediate portions. The fuel pipes 12 and 13 are respectively connected to the fuel system provided between the fuel tank and the fuel injector of the vehicle by means of connectors (not shown), which are fixed to the claws 18 and 19. As a result, fuel is supplied into the fuel passages 14 and 15 of the fuel pipes 12 and 13, so that the fuel flows into the fuel chamber 11 formed in the first housing member 10 from the fuel passage 14, and flows out of the fuel chamber 11 into the fuel passage 15.

The first electrode 40 is made of a metal, such as stainless steel, and formed in a cylindrical shape. The first electrode 40 is inserted into the fuel chamber 11 of the first housing member 10 through an open end 29 of an insertion hole 20, which is formed at a side wall of the first housing member 10 in such a way that the insertion hole 20 extends in a radial direction of the first housing member 10 so as to communicate the fuel chamber 11 with an outside area of the first housing member 10.

The first electrode 40 is composed of a cylindrical portion 41 accommodated in the fuel chamber 11 of the first housing member 10, a middle-diameter portion 42 (e.g., a first diameter portion into the insertion hole 20 of the first housing member 10 and having an outer diameter larger than that of the cylindrical portion 41, and a large-diameter portion 43 (e.g., a second diameter portion) having an outer diameter larger than that of the middle-diameter portion 42. Fuel ports 44 and 45 are formed at the cylindrical portion 41 in a radial direction thereof so as to communicate a space formed at an outer surface of the cylindrical portion 41 (that is, the fuel chamber 11) with a space formed at an inner surface of the cylindrical portion 41 (that is, an inside space of the cylindrical portion 41). Accordingly, the fuel flows from the fuel chamber 11 of the first housing member 10 into an inside space 46 of the first electrode 40 through the fuel port 44 and flows out of the inside space 46 though the port 45. A lower end of the cylindrical portion 41, which is opposite to the large-diameter portion 43, is inserted into a recessed portion 21 formed at an inner surface of the first housing member 10, which is opposite to the insertion hole 20 in the radial direction of the first housing member 10. A small gap (not shown) is formed between the lower end of the cylindrical portion 41 and the recessed portion 21.

An inner wall of the insertion hole 20 of the first housing member 10 corresponds to the middle-diameter and large-diameter portions 42 and 43 of the first electrode 40. Therefore, an inner diameter of the inner wall is changed at an intermediate portion thereof. The inner wall of the insertion hole 20 of the first housing member 10 has a first vertical surface 22 and a first stepped surface 23, which correspond to the large-diameter portion 43 of the first electrode 40, wherein the first vertical surface 22 is perpendicular to an axis of the first housing member 10 and the first stepped surface 23 is in parallel to the axis of the first housing member 10. The inner wall of the insertion hole 20 further has a second vertical surface 24 and a second stepped surface 25, which likewise correspond to the middle-diameter portion 42 of the first electrode 40, wherein the second vertical surface 24 is perpendicular to the axis of the first housing member 10 and the second stepped surface 25 is in parallel to the axis of the first housing member 10.

The first stepped surface 23 (which is also referred to as a sealing surface) is a part of the inner wall of the insertion hole 20, which is formed at an opposite side to the open end 29 of the insertion hole 20. In other words, the sealing surface 23 opposing to the open end 29 of the insertion hole 20 is brought into a fluid-tight contact with a lower-side surface of the large-diameter portion 43 facing toward the fuel chamber 11. A small gap is formed between a radially-outward surface of the large-diameter portion 43 and the first vertical surface 22. Furthermore, small gaps are formed between the middle-diameter portion 42 (a radially-outward surface thereof) and the second vertical surface 24 and between the middle-diameter portion 42 (a lower-side surface thereof facing toward the fuel chamber 11) and the second stepped surface 25.

The second electrode 50 is made of a metal, such as stainless steel, and formed in a cylindrical shape having a closed bottom portion. The second electrode 50 is accommodated in the inside space 46 of the first electrode 40. A radially-outward wall of the second electrode 50, more exactly, an outer wall of a lower part of the second electrode 50, is exposed to the fuel filled in the inside space 46, because the fuel flows from the fuel chamber 11 of the first housing member 10 into the inside space 46.

A glass seal 51 of a cylindrical shape is firmly provided as an insulating member between the radially-outward wall of the second electrode 50 and radially-inward walls of the large-diameter and middle-diameter portions 43 and 42. Accordingly, the first electrode 40 and the second electrode 50 are formed as an integrated one unit. The glass seal 51 electrically insulates the first electrode 40 and the second electrode 50 from each other.

The thermister 52, working as a temperature sensor, is composed of a temperature sensing element, electrical resistance of which varies depending on temperature change. The thermister 52 is disposed inside the second electrode 50 so that it is in contact with an inner surface of the closed bottom portion of the second electrode 50. Temperature of the fuel flowing around the second electrode 50 is transmitted to the thermister 52 via the second electrode 50. Thus, the thermistor 52 detects the temperature of the fuel flowing between the first and second electrodes 40 and 50.

The second housing member 30 is made of resin, for example, and formed in a cylindrical form having a closed bottom portion. An outer bottom surface 31 of the second housing member 30 is brought into contact with an outer wall surface 26 of the first housing member 10. The open end 29 of the insertion hole 20 is formed at the outer wall surface 26 of the first housing member 10, and the open end 29 is closed by the outer bottom surface 31 of the second housing member 30. The second housing member 30 is fixed to the first housing member 10, for example, by screws (not shown) which are inserted and screwed into the first housing member 10 from an inner side of the closed bottom portion of the second housing member 30.

A groove 27 is formed at the outer wall surface 26 of the first housing member 10 so as to surround the open end 29 of the insertion hole 20. A packing 33 is disposed between the groove 27 and the outer bottom surface 31 of the second housing member 30, so that the packing 33 is inserted into and compressed in the grove 27 in order to prevent water from coming into inside from outside.

A cover plate 34 is attached to an open end 39 of the second housing member 30 in order to prevent water from coming into inside from outside. The cover plate 34 is pressed and firmly attached to the open end 39 of the second housing member 30 by plate-shaped springs 36 formed at a lock member 35, which extends radially outwardly of the second housing member 30.

An accommodation hole 37 is formed at the closed bottom portion of the second housing member 30 for accommodating an upper open end portion of the second electrode 50. A small gap is formed between an inner surface of the accommodation hole 37 and the outer surface (the radially-outward wall) of the second electrode 50.

The electric circuit (the electronic control unit) 60 is accommodated in the second housing member 30 and is composed of a micro-computer, ICs, electric parts such as resisters, and so on, which are assembled to a printed circuit board. A first electric conductive member 61 and a second electric conductive member 62 (hereinafter also referred to as first and second terminals) electrically connect the first and second electrodes 40 and 50 to the electric circuit 60, respectively. A third and a fourth electric conductive member 63 and 64 (third and fourth terminals) electrically connect the thermister 52 to the electric circuit 60. As a result, the electric circuit 60 detects electrostatic capacity between the first and second electrodes 40 and 50. In addition, the electric circuit 60 corrects a value of the electrostatic capacity based on the fuel temperature detected by the thermister 52, in order to detect the ethanol density contained in the fuel.

A connector (not shown) is provided at the second housing member 30, so that the ethanol density of the fuel detected by the electric circuit 60 is transmitted to the ECU (not shown) via the connector.

A first elastic member 70, which is made of a plate-shaped rubber, for example, having a coefficient of thermal conductivity smaller than those of the second housing member 30 and the first electrode 40, is disposed between the first electrode 40 and a recess 38 formed at the outer bottom surface 31 of the second housing member 30. As a result, the lower-side surface of the large-diameter portion 43 of the first electrode 40, which is the surface facing toward the fuel chamber 11, is pressed against the first stepped surface (the sealing surface) 23 of the first housing member 10. A diameter of the recess 38 of the second housing member 30 is made larger than that of the large-diameter portion 43 of the first electrode 40. Therefore, the first elastic member 70 seals the small gap formed between the radially-outward surface of the large-diameter portion 43 and the first vertical surface 22 of the first housing member 10. A circular hole 71 is formed in the first elastic member 70, and an inner surface of the circular hole 71 is fluid-tightly in contact with the radially-outward wall of the second electrode 50.

When electric power is applied from the ECU to the second electrode 50 through the electric circuit 60, the electrostatic capacity is formed between the first and second electrodes 40 and 50. The value of the electrostatic capacity varies depending on specific inductive capacity of the fuel. The specific inductive capacity of gasoline is roughly between 2.0 and 2.2, while the specific inductive capacity of ethanol is about 24.5. And those specific inductive capacities vary depending on temperature change. Accordingly, the electrostatic capacity to be detected by the electric circuit 60 varies depending on not only a mixing ratio of gasoline and ethanol in the fuel but also temperature of the fuel.

The electric circuit 60 corrects the value of the electrostatic capacity between the first and second electrodes 40 and 50 based on the fuel temperature detected by the thermister 52, so as to detect the ethanol density contained in the fuel. The ethanol density of the fuel detected by the electric circuit 60 is transmitted to the ECU. The ECU decides the fuel injection amount as well as the fuel injection timing based on the ethanol density of the fuel.

According to the first embodiment, the first elastic member 70 presses the first electrode 40 toward the first housing member 10, so that the lower-side surface of the large-diameter portion 43 facing toward the fuel chamber 11 is pressed against the first stepped surface (the sealing surface) 23 of the first housing member 10. The second housing member 30 is made of the resin, while the first electrode 40 is made of the metal. A gap may be generated between the second housing member 30 and the first electrode 40 due to different coefficients of thermal expansion. However, the generation of such gap is suppressed by the first elastic member 70. And thereby, it is possible to prevent a disconnection of the first terminal 61, which connects the first electrode 40 to the electric circuit 60.

In addition, there is concern that the second terminal 62 for connecting the second electrode 50 to the electric circuit 60 may be disconnected, when the gap may be generated between the second housing member 30 and the first electrode 40, because the second electrode 50 is firmly fixed to the first electrode 40 by means of the glass seal 51. However, as explained above, the first elastic member 70 can suppress the generation of the gap between the second housing member 30 and the first electrode 40, and thereby it is also possible to prevent a disconnection of the second terminal 62, which connects the second electrode 50 to the electric circuit 60.

Furthermore, according to the present embodiment, the first elastic member 70 is arranged between the recess 38 of the second housing member 30 and the first electrode 40. The first elastic member 70 can absorb mechanical shock applied to the first and second housing members 10 and 30 in an axial direction of the first electrode 40, when any external force may be applied to the first and/or second housing members 10 and 30, for example, as a result that the sensor 1 is dropped during transportation or an assembling process. Thereby, it is possible to prevent the glass seal 51 (which is firmly connecting the first and second electrodes 40 and 50) from being broken or prevent a crack from being generated in the glass seal 51.

Furthermore, according to the present embodiment, the first elastic member 70 suppresses thermal conduction between the second housing member 30 and the first electrode 40 or between the second housing member 30 and the glass seal 51. As a result, the thermal conduction of the heat generated at the electric circuit 60 to the second electrode 50 via the second housing member 30, the first electrode 40 and the glass seal 51 may be suppressed. And thereby, it is possible that the thermister 52 accurately detects the temperature of the fuel between the first and second electrodes 40 and 50, wherein the heat of the fuel between the first and second electrodes 40 and 50 is transmitted to the thermister 52 via the second electrode 50. Accordingly, the electric circuit 60 can accurately detect the ethanol density contained in the fuel.

(Second Embodiment)

Figure 3:
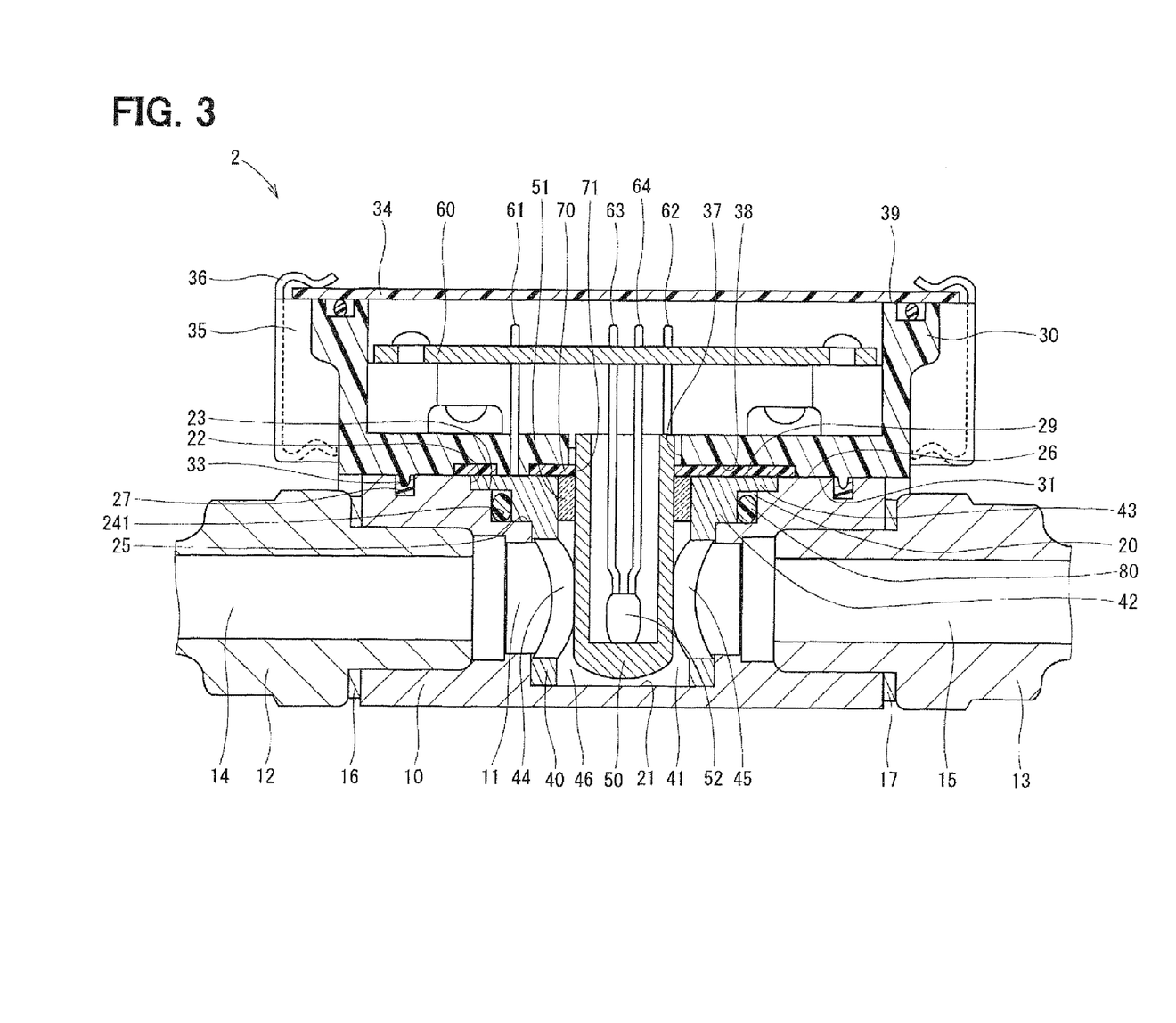
FIG. 3 is a schematic enlarged cross-sectional view showing a relevant portion of a fuel-aspect sensor according to a second embodiment of the present invention.

FIG. 3 shows a fuel-aspect sensor according to a second embodiment of the present invention. The same reference numerals are used for such portions of the second embodiment, which are the same or substantially similar to those of the first embodiment, and the explanation thereof is omitted. According to the fuel-aspect sensor 2 of the present embodiment, an annular space is formed between a radially-outward surface of the middle-diameter portion 42 of the first electrode 40 and a second vertical surface 241 of the first housing member 10, so that a second elastic member 80 is arranged in the annular space. The second elastic member 80 is made of a ring-shaped rubber, for example, which has a coefficient of thermal conductivity smaller than those of the first housing member 10 and the first electrode 40. The second elastic member 80 is formed in a circular shape in its cross section. The second elastic member 80 is fluid-tightly in contact with the radially-outward surface of the middle-diameter portion 42 of the first electrode 40 and the second vertical surface 241 of the first housing member 10, so as to prevent the fuel from leaking through the space between the first housing member 10 and the first electrode 40.

According to the present embodiment, the second elastic member 80 is arranged at a position, which is away from the glass seal 51 in a radially-outward direction thereof. Therefore, the second elastic member 80 can absorb mechanical shock applied to the first and/or second housing members 10 and 30 in a radial direction of the first electrode 40, when any external force may be applied to the first and/or second housing members 10 and 30, or to the fuel pipes 12 and 13, for example, as a result that the sensor 2 is dropped during transportation or an assembling process. As above, it is possible to surely prevent the glass seal 51 (which is firmly connecting the first and second electrodes 40 and 50) from being broken or prevent a crack from being generated in the glass seal 51.

Furthermore, according to the present embodiment, the second elastic member 80 is arranged between the first housing member 10 and the first electrode 40, so that the second elastic member 80 suppresses thermal conduction between the first housing member 10 and the first electrode 40. Namely, the thermal conduction of the heat generated at the electric circuit 60 to the second electrode 50 via the second housing member 30, the first electrode 40 and the glass seal 51 may be suppressed. In the same manner to the first embodiment, it is possible that the thermister 52 accurately detects the temperature of the fuel between the first and second electrodes 40 and 50, wherein the heat of the fuel between the first and second electrodes 40 and 50 is transmitted to the thermister 52 via the second electrode 50. The detection accuracy of the fuel-aspect sensor 2 is thereby improved.

(Other Embodiments)

In the above embodiments, the first and second elastic members 70 and 80 are made of rubber. However, the elastic members 70 and 80 may be made of resin. In addition, air bubbles may be formed in the elastic members so as to make coefficient of thermal conductivity much smaller.

In the above embodiments, the sensors are applied to the fuel-aspect sensors for detecting ethanol density contained in the fuel. The present invention may be also applied to any other types of fuel-aspect sensors for detecting aspects of mixed fuel, which is mixture of different fuels respectively having different specific inductive capacities.

As above, the present invention should not be limited to the embodiments described above, but may be modified in various ways without departing from the principle of the invention.

What is claimed is:

1. A fuel-aspect sensor for detecting aspects of mixed fuel, which is mixture of different fuels respectively having different specific inductive capacities, comprising:
    a first housing member having a fuel chamber through which the mixed fuel flows and an insertion hole for communicating the fuel chamber with outside of the first housing member, the insertion hole having an open end at which a stepped portion is formed;
    a first electrode inserted into the insertion hole from the open end of the insertion hole, the first electrode having an inside space being in communication with the fuel chamber, the first electrode having a flanged portion extending in a radial direction of the first electrode so that the flanged portion is inserted into the stepped portion of the insertion hole;
    a second electrode having a closed bottom portion, a lower part of the second electrode being accommodated in the inside space of the first electrode, so that an outer surface of the second electrode is exposed to the mixed fuel introduced into the inside space of the first electrode;
    an insulating member for electrically insulating the first and second electrodes from each other and for firmly fixing the first and second electrodes to each other;
    a temperature sensor accommodated in the second electrode and fixed to an inside surface of the closed bottom portion thereof for detecting temperature of the mixed fuel;
    a second housing member firmly attached to the first housing member for closing the open end of the insertion hole of the first housing member;
    an electronic control unit accommodated in the second housing member and electrically connected to the first electrode, the second electrode, and the temperature sensor, for detecting electrostatic capacity between the first and second electrodes, to thereby detect the aspects of the mixed fuel based on the electrostatic capacity and the temperature of the mixed fuel; and
    an elastic member disposed between the second housing member and the first electrode for biasing the flanged portion of the first electrode toward a sealing surface of the first housing member, which is formed at an inner wall of the insertion hole, so that the flanged portion is in contact with the sealing surface,
    wherein a diameter of the elastic member is larger than that of the flanged portion of the first electrode,
    wherein the stepped portion comprises a first vertical surface, a first stepped surface, a second vertical surface, and a second stepped surface, and
    wherein the flanged portion comprises a first diameter portion and a second diameter portion, in which the second diameter portion is larger than the first diameter portion.

2. The fuel-aspect sensor according to the claim 1, wherein the elastic member is made of such material having coefficient of thermal conductivity smaller than those of the second housing member and the first electrode.

3. The fuel-aspect sensor according to the claim 1, wherein the sealing surface of the first housing member is formed as a stepped surface at the inner wall of the insertion hole, which is perpendicular to a direction in which the first electrode is biased by the elastic member.

4. The fuel-aspect sensor according to the claim 1, wherein the elastic member is accommodated in a recess formed at an outer bottom surface of the second housing member, and
    a circular hole is formed in the elastic member, through which an open-end side of the second electrode is inserted, so that an inner surface of the circular hole is fluid-tightly in contact with a radially-outward wall of the open-end side of the second electrode.

5. The fuel-aspect sensor according to the claim 1, wherein the insulating member is formed in a cylindrical shape, and
    a ring-shaped elastic member is arranged at a position, which is away from the insulating member in a radially-outward direction thereof, and the ring-shaped elastic member being arranged between the first electrode and the first housing member.

6. The fuel-aspect sensor according to the claim 1, further comprising:
    fuel pipes for supplying the fuel into the fuel chamber and discharging the fuel from the fuel chamber.

7. A fuel-aspect sensor for detecting aspects of mixed fuel, which is mixture of different fuels respectively having different specific inductive capacities, comprising:
    a first housing member having a fuel chamber through which the mixed fuel flows and an insertion hole for communicating the fuel chamber with outside of the first housing member, the first housing member having a first axial end connected to a first fuel pipe to be connected to a fuel tank and a second axial end connected to a second fuel pipe to be connected to an engine;
    a first electrode inserted into the insertion hole from an open end of the insertion hole, the first electrode having an inside space being in communication with the fuel chamber;
    a second electrode having a closed bottom portion, a lower part of the second electrode being accommodated in the inside space of the first electrode, so that an outer surface of the second electrode is exposed to the mixed fuel introduced into the inside space of the first electrode;
    an insulating member for electrically insulating the first and second electrodes from each other and for firmly fixing the first and second electrodes to each other;
    a temperature sensor accommodated in the second electrode and fixed to an inside surface of the closed bottom portion thereof for detecting temperature of the mixed fuel;
    a second housing member firmly attached to the first housing member for closing the open end of the insertion hole of the first housing member;
    an electronic control unit accommodated in the second housing member and electrically connected to the first electrode, the second electrode, and the temperature sensor, for detecting electrostatic capacity between the first and second electrodes, to thereby detect the aspects of the mixed fuel based on the electrostatic capacity and the temperature of the mixed fuel; and
    an elastic member disposed between the second housing member and the first electrode for biasing the first electrode toward a sealing surface of the first housing member, which is formed at an inner wall of the insertion hole so as to oppose to the open end of the hole.

* * * * *